(12) United States Patent
Fuller

(10) Patent No.: US 9,993,800 B2
(45) Date of Patent: Jun. 12, 2018

(54) OXYGEN UPTAKE COMPOSITIONS AND PRESERVATION OF OXYGEN PERISHABLE GOODS

(71) Applicant: JP Patents, L.L.C., Park City, UT (US)

(72) Inventor: Peter E. Fuller, Park City, UT (US)

(73) Assignee: JP Patents L.L.C., Park City, UT (US)

( * ) Notice: Subject to any disclaimer, the term of this patent is extended or adjusted under 35 U.S.C. 154(b) by 0 days. days.

(21) Appl. No.: 15/084,264

(22) Filed: Mar. 29, 2016

(65) Prior Publication Data

US 2017/0021331 A1    Jan. 26, 2017

Related U.S. Application Data

(62) Division of application No. 14/473,569, filed on Aug. 29, 2014, now Pat. No. 9,326,501.

(Continued)

(51) Int. Cl.
| | |
|---|---|
| *B01J 20/04* | (2006.01) |
| *B01J 20/22* | (2006.01) |
| *A23L 3/3508* | (2006.01) |
| *A01N 1/02* | (2006.01) |
| *A23L 3/3436* | (2006.01) |

(Continued)

(52) U.S. Cl.
CPC .............. *B01J 20/22* (2013.01); *A01N 1/021* (2013.01); *A01N 3/00* (2013.01); *A01N 59/04* (2013.01); *A23B 4/16* (2013.01); *A23B 7/148* (2013.01); *A23L 3/3436* (2013.01); *A23L 3/358* (2013.01); *A23L 3/3508* (2013.01); *B01J 20/043* (2013.01);

(Continued)

(58) Field of Classification Search
CPC ................................ B01J 20/043; B01J 20/22
See application file for complete search history.

(56) References Cited

U.S. PATENT DOCUMENTS

| | | |
|---|---|---|
| 4,708,886 A | 11/1987 | Nelson |
| 4,913,942 A | 4/1990 | Jick |

(Continued)

FOREIGN PATENT DOCUMENTS

WO    WO 2012/156685 A2    11/2012

OTHER PUBLICATIONS

Master-Bilt Refrigeration Solutions (Oct. 2010) *Cool It! Defrosting Basics & Beyond* 11(4), 1-2.

(Continued)

*Primary Examiner* — Rosanne Kosson
(74) *Attorney, Agent, or Firm* — Thorpe North & Western, LLP

(57) ABSTRACT

The preservation or extension of the life of oxygen perishable products such as fresh or cooked meats; fresh vegetables and fruits; dried vegetables, fruits and meats; packaged pharmaceuticals or biologicals; open and enclosed marketing display cases of meats, fruits and vegetables; and packaging, warehousing and transportation of meats, fruits, and vegetables is obtained by subjecting such products to an atmosphere obtained from gas permeable packets of an oxygen scavenging composition comprising a sodium carbonate mineral and one or more carboxylic acids. When the environment surrounding the oxygen perishable product is subjected to the packets of gaseous permeable oxygen scavenging compositions, oxygen is taken in by the scavenging composition and also the presence of carbon dioxide in the surrounding environment is enhanced thereby minimizing or eliminating the effect the oxygen on the oxygen perishable products.

15 Claims, 12 Drawing Sheets

Related U.S. Application Data

(60) Provisional application No. 61/872,783, filed on Sep. 2, 2013.

(51) Int. Cl.
    *A23L 3/358*    (2006.01)
    *A23B 4/16*     (2006.01)
    *A23B 7/148*    (2006.01)
    *A01N 3/00*     (2006.01)
    *A01N 59/04*    (2006.01)
    *B01J 20/28*    (2006.01)

(52) U.S. Cl.
    CPC ..... *B01J 20/2805* (2013.01); *B01J 20/28016* (2013.01); *A23V 2002/00* (2013.01)

(56) References Cited

U.S. PATENT DOCUMENTS

| | | |
|---|---|---|
| 5,236,617 A | 8/1993 | Ueno et al. |
| 5,752,390 A | 5/1998 | Hyde |
| 6,106,775 A | 8/2000 | Fuller |
| 6,264,740 B1 | 7/2001 | McNulty, Jr. |
| 6,274,304 B1 | 8/2001 | Buschek et al. |
| 6,447,826 B1 | 9/2002 | Matthews |
| 7,387,205 B1 | 6/2008 | Wilson |
| 2001/0031298 A1 | 10/2001 | Fuller |
| 2004/0242746 A1 | 12/2004 | Freedman et al. |
| 2004/0247750 A1 | 12/2004 | Finnegan et al. |
| 2007/0041885 A1 | 2/2007 | Maziuk |
| 2010/0031853 A1 | 2/2010 | Visocekas et al. |
| 2010/0047405 A1 | 2/2010 | Versteylen et al. |
| 2012/0301409 A1 | 11/2012 | Jensen et al. |
| 2014/0106002 A1 | 4/2014 | Jensen et al. |

OTHER PUBLICATIONS

Nitro-pack.com (2013) Product 389—Oxygen Absorbers— 50 Pak; https://www.nitro-pak.com ; accessed online Jul. 2, 2013; 2 pages.

Wheatgrasskits.com (2013) Oxy Free; Oxygen Absorbers Packets; http://wheatgrasskits.com/oxygen_absorbers. html?gdftrk=gdfV21874_a_7c241_a_7c . . . ; accessed online Jul. 2, 2013; 2 pages.

Wikipedia Foundation Inc. (2013) *Oxygen absorber Wikipedia* http://en.wikipedia.org/wiki/Oxygen_absorber ; accessed online Jul. 2, 2013; 2 pages.

OXYGEN UPTAKE COMPOSITIONS AND PRESERVATION OF OXYGEN PERISHABLE GOODS

RELATED APPLICATIONS

This application claims the benefit of U.S. application Ser. No. 14/473,569, filed Aug. 29, 2014, which claims priority to U.S. Provisional Application No. 61/872,783, filed Sep. 2, 2013, which are each incorporated herein by reference.

FIELD OF THE INVENTION

The present invention relates to novel oxygen uptake compositions comprising the mineral trona and a mono-, di- or tri-carboxylic acid, that are useful in the uptake of oxygen from a surrounding atmosphere of oxygen perishable products by adsorption of oxygen onto the surface of the trona/carboxylic acid or scavenging oxygen from the surrounding atmosphere and converting such oxygen into carbon dioxide gas to provide an inert environment for oxygen perishable goods. More specifically, the present invention relates to the use of the mineral trona, comprising sodium carbonate and sodium bicarbonate, in combination with a mono-, di- or tri-carboxylic acid for the preservation or pacification of oxygen perishable goods by the adsorption of oxygen onto the trona/carboxylic acid surface and/or the conversion of oxygen into carbon dioxide resulting in the preservation of goods that are subject to oxygen degradation for prolonged periods of time.

BACKGROUND OF THE INVENTION

Oxygen is essential for sustaining of all aerobic living matter which is inclusive of essentially all known forms of animal and plant life. In humans and other forms of animal life, generally the respiratory cycle comprises breathing in of oxygen which is absorbed in the lungs and distributed accordingly in the blood, to various organs and is eventually "used" up, i.e. exchanged or converted to carbon dioxide by various body interactions and exhaled from the lungs primarily as carbon dioxide or other expiratory gases.

On the other hand, plant life is dependent upon carbon dioxide and takes it in where, through photosynthesis, it is metabolized or used by the plant in various processes and is eventually converted and released into the atmosphere as oxygen.

This life cycle is essential to the living planet and all living species is well documented and will not be further addressed in this specification.

However, each of these gasses has downsides as well. Oxygen participates in or causes the degradation of organic materials to which it has been exposed. This is particularly true with perishable organic materials such as fruits, vegetables, grains, meat products, processed foods, powdered products such as flour, pharmaceuticals, and the like which may be in an atmosphere maintained at ambient temperatures or above. In other words, the lowering of temperatures and lessening or removal of available oxygen content contributes to lengthening the useful life of such materials. Refrigeration is a common mechanism used to extend useful life of perishable goods. Unfortunately, refrigeration also utilizes substantial amounts of energy to maintain suitably low temperatures to achieve desired results.

Oxygen perishable items from the time of gathering or production, whether by reaping, picking, digging, cutting, collecting, butchering, processing, cooking, displaying, packaging or any other means, where such items are present in an open environment for a period of time, are subject to being exposed to oxygen. Surrounding environments are those present when gathering perishables by any of the above methods as well as loading, transporting, warehousing, manufacturing or processing, packaging in crates or other shipping containers for overland or sea transport, packaging or sealing in containers for sale, refrigerated shipping or storage, cooling and sectioning of butchered animals and the like. An open environment is also inclusive of enclosed or semi-enclosed spaces such as found in display counters holding fruits, meats or vegetable in retail outlets.

Therefore, perishable items may be presented for sale, use or distribution as counter displays, refrigerated fruit, vegetable and flower stands, refrigerated retail displays for meats and processed foods, packaged and sealed dry goods such as grains, processed grains such as flour, manufactured pharmaceuticals, blood and blood products and organs for organ transplants, or any other approach when presented for harvesting, transportation, processing, packaging, displaying or selling. Similar or equivalent but unmentioned modes of treating any other oxygen perishable items are to be included.

Subjecting of perishable items to an open atmosphere in the presence of oxygen and particularly when at ambient or elevated temperatures causes the perishable items to lose freshness and texture, decay, produce objectionable odors, and become inedible, unsalable or unusable. To rectify this, means and methods have been sought to lessen the objectionable results and extend the useful life of perishable items. Most decay or spoilage of perishable items is the result of growth of aerobic microorganisms or pathogens including bacteria, fungi, viruses, which are of animal or vegetable origin.

U.S. Pat. No. 6,106,775, issued Aug. 22, 2001 discloses devices and methods for introducing humidity into an atmosphere. The device comprises an apertured shell containing an absorbent material inside which can absorb and retain water. Evaporation of water is enhanced by placing a mixture of sodium bicarbonate and acetylsalicylic acid (aspirin) on the absorbent material. The purpose is to humidify produce bins, refrigerated produce containers, cheese and meat refrigerators and containers of dry food, such as cookies and brown sugar.

Published U.S. Application 20010031298, published Oct. 18, 2001, is indirectly a continuation-in-part of U.S. Pat. No. 6,106,775, and teaches the use of aqueous compositions containing a combination of sodium bicarbonate and acetylsalicylic acid (aspirin) to maintain relatively high levels of carbon dioxide in the atmosphere of selected environments to prolong the shelf life of various perishable foods and products such as vegetables, fruits, meats, fish, seafood, dairy products and dry goods. The aqueous composition can be applied by directly bathing or showering a perishable product in the aqueous composition or indirectly using absorption devices that carry the aqueous compositions placed in close proximity to a perishable product.

Currently the favored means is by using suitable oxygen absorbers to prevent oxygen from destroying or rendering perishable items unsalable or useless. Most oxygen absorbers presently used are based on iron powder, iron oxides or iron salts which react with oxygen in the surrounding atmosphere causing the iron powder or salt to oxidize, further oxidize or rust. When all the iron has oxidized the oxygen absorbers are loaded and cease to function. The iron containing powder is packaged in plastic bags which are permeable to oxygen. The iron containing powder may be formulated with activated charcoal, and salts to further absorb oxygen or hasten its conversion to an iron oxide.

These oxygen absorbers are not edible and have limited life span when exposed to the atmosphere. They function best when used in a sealed or closed environment such as in dry pack canning but are not suitable for fresh produce such as fruits, vegetables, freshly cut and or packaged meats. In such situations, where oxygen may be present in the surrounding environment, iron based absorbers have limited utility. Further, iron oxygen absorbers often leave a metallic taste in produce, grains and other products where they have been utilized in a sealed environment for an extended period of time.

In view of the foregoing, there is a need for advancements in the art for compositions and methods providing innovative techniques for preserving oxygen perishable products. It would be particularly useful if such preservation compositions and techniques could be used at ambient or refrigerated conditions and be endothermic in nature to minimize or preserve ambient temperatures for the extended life of oxygen perishable products. It would also be advantageous to provide preservation systems and methods that are cost efficient and are safe for use with foods intended for animal and particularly human consumption. Any increase in the shelf life of oxygen perishable products, such as foods, could have great benefit for many entities involved in the relevant industries, including growers, transporters, retail outlets such as markets, food outlets, and, ultimately, consumers

SUMMARY OF THE INVENTION

The present invention relates to chemical compositions and associated apparatus and methods for the uptake of oxygen from oxygen perishable products or from within the vicinity of such products and generating and releasing carbon dioxide into the atmosphere surrounding said products. The oxygen may be either adsorbed on the surface of such compositions or absorbed by such compositions. In either event oxygen within the vicinity of oxygen perishable products is taken up either by being absorbed or adsorbed by a trona/carboxylic acid combination and is converted into carbon dioxide thereby preserving a life or freshness of the oxygen perishable products. Here the term "oxygen uptake" is used in reference to the trona/acid compositions and is inclusive of absorption, adsorption or any other means by which oxygen concentration in the atmosphere surrounding the oxygen perishable goods is lessened or eliminated. Therefore, as used in this disclosure, the terms oxygen uptake and oxygen absorber/oxygen adsorber and the like may be used interchangeably.

Trona is a natural mineral composed mainly of sodium carbonate and sodium bicarbonate and is chemically referred to as trisodium hydrogendicarbonate dehydrate or sodium sesquicarbonate, having the formula: $Na_3(CO_3)(HCO_3).2H_2O$. Trona is generally mined from salt lake deposits which can be found in the United States, Africa, China, Turkey, and Mexico. Large stratified deposits are mined in Sweetwater County, Wyo. Other trona deposits are also found in the states of Nevada and California in the United States. Mined trona can be found in, or processed into, various degrees of purification. Some trona may contain minute amounts of potassium carbonate and potassium bicarbonate with even lesser amounts of magnesium and calcium salts and other trace minerals.

Other sodium carbonate minerals, somewhat similar to trona, include gaylussite, natron, prissonite, northupite, nahcolite and thermonatrite. To the extent these sodium carbonate containing minerals are functionally used in place of, or as a substitute for trona, they are deemed to be within the scope of this invention. Therefore, the term "sodium carbonate mineral or minerals" as used herein generically will be inclusive of trona, gaylussite, natron, prissonite, northupite, nahcolite and thermonatrite, including combinations of these minerals. These sodium carbonate minerals all have an oxygen adsorbing and/or absorbing capability suitable for use in the present invention.

Trona is a particularly useful sodium carbonate mineral having oxygen adsorbing, or absorbing characteristics and is made up primarily of trisodium hydrogendicarbonate dihydrate, $[Na_3(CO_3)(HCO_3).2H_2O]$ as the primary active ingredients. The only intended limitation in defining trona is that of functionality including oxygen uptake, i.e. adsorption and/or absorption. To that extent, for purposes of this disclosure, trona and hydrogendicarbonate dihydrate may be used interchangeably. Further, all discussion involving trona is also applicable to other sodium carbonate minerals listed herein and should be considered fully disclosed as suitable alternatives to trona.

Although not required, the sodium carbonate mineral can be recovered and used directly, e.g. without calcining, recrystallization, purification, etc. In some cases, the sodium carbonate mineral can be separated from rock or other debris, however can typically be used without substantive modification of the native mineral other than crushing to a suitable size.

Trona may sometimes be referred to in older literature as urao or nitrum. Trona is generally processed or purified by calcination to obtain soda ash or sodium carbonate $(Na_2CO_3)$ and is used primarily in glass manufacture. Trona is also used in many other applications ranging from animal feed, chemical manufacture, and medicine.

The mono-, di- or tricarboxylic acids that can be utilized may contain from two to twenty carbon atoms and can be formed of straight, branched, saturated or unsaturated carbon chains and, aromatic moieties and be substituted or unsubstituted.

The chemical compositions comprise a novel combination of the mineral trona and one or more mono-, di- or tri-carboxylic acids in appropriate proportions. Trona contains, as primary ingredients, a mixture of sodium carbonate and sodium bicarbonate along with minor amounts of other minerals or mineral salts as noted above. When the combination of trona and the carboxylic acid are brought together, optionally in the presence of moisture, an acid/base reaction occurs and carbon dioxide is produced. Also, testing has shown that when trona and a carboxylic acid, in the presence of moisture, are brought together in an oxygen containing environment, oxygen is taken up by the reaction and the concentration of oxygen is diminished or essentially eliminated. This is particularly relevant when the reaction takes place in the presence of oxygen perishable goods. It is postulated that the solid trona/carboxylic acid composition not only reacts in the presence of moisture but also serves as an oxygen adsorber or absorber with oxygen being adsorbed on the surface of the trona crystals by chemical adsorption and/or absorbed into the trona/carboxylic acid combination where it chemically interacts with some or all of the components in the mixture to cause the oxygen to be converted into carbon dioxide. Presumably the carbonates present in the trona/acid mixture provide the carbon necessary for the oxygen conversion into carbon dioxide. Laboratory tests, as well as testing in the presence of oxygen perishable goods, shows diminished oxygen content, preservation of oxygen perishable goods as will be further delineated in this disclosure.

BRIEF DESCRIPTION OF THE DRAWINGS

In order that the manner in which the invention, including methods, uses, apparatus, devices or any other means recited, are to be carried out to obtain the desired advantages and results set forth herein, a more particular description of the invention is illustrated in the attached drawing and the written description which follows. It is to be understood that these drawings depict only representative embodiments of the invention and are not to be considered as limiting the scope which is limited only by the attached claims and functional equivalents thereof.

DETAILED DESCRIPTION OF THE INVENTION

Figure 1:
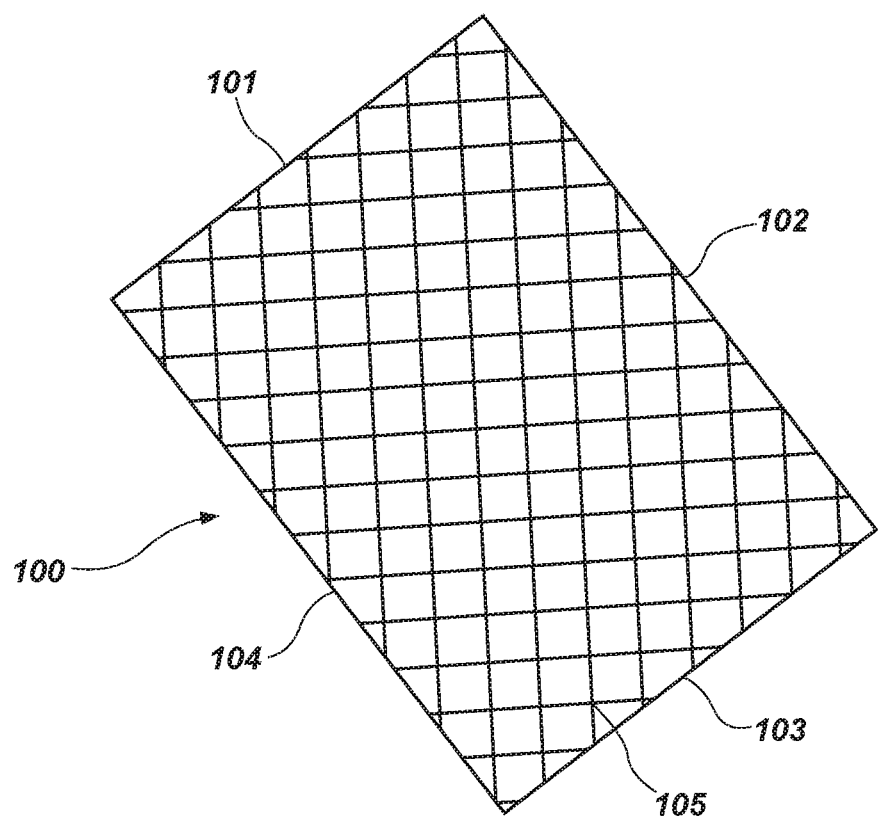
FIG. 1 is a perspective view of a liquid or gas permeable woven packet of the invention containing a mixture of trona and one or more mon-, di- or tri-carboxylic acids.

The mineral trona has been described above and such description, to the extent necessary, is incorporated herein.

The carboxylic acids may be any of a wide variety of mono-, di- and tricarboxylic acids. These carboxylic acids may be comprised of mono-, di- or tricarboxylic acids having the general formula:

$$(HOOC)-R-(COOH)_{x-1}$$

where x is an integer of 1, 2 or 3, and R is a saturated or unsaturated, straight, or branched carbon chain having one to eighteen carbon atoms, or an aromatic moiety having six to eighteen carbon atoms which may be substituted or unsubstituted by OH, COOH, COOM, COOR', —OR' substituents, where M can be an alkali or alkaline earth metal, and where R' can be saturated or unsaturated, straight, or branched carbon chain having from one to eight carbons, an aromatic moiety having six to eighteen carbon atoms which may be substituted by alkyl groups having one to eight carbons, OH, COOH, COOM, COOR', —OR' substituents, and M can be an alkali or alkaline earth metal. For purposes described herein salicylic acid and citric acid are particularly useful carboxylic acids with citric acid providing exceptional results, although other carboxylic acids can also be used. Suitable carboxylic acids can be used singly or in combination with multiple carboxylic acids. Representative, but not inclusive, of such carboxylic acids are found in the following listings.

Representative of monocarboxylic saturated and unsaturated acids are:

| | |
|---|---|
| $CH_3CO_2H$ | acetic acid |
| $CH_3CH_2CO_2H$ | propionic acid |
| $CH_3(CH_2)_2CO_2H$ | butyric acid |
| $CH(CH_2)_3CO_2H$ | valeric acid |
| $CH_3(CH_2)_4CO_2H$ | caproic acid |
| $CH(CH_2)_6CO_2H$ | caprylic acid |
| $CH_3(CH_2)_8CO_2H$ | capric acid |
| $CH_3(CH_2)_{10}COOH$ | Lauric acid |
| $CH_3(CH_2)_{12}COOH$ | Myristic acid |
| $CH_3(CH_2)_{14}COOH$ | Palmitic acid |
| $CH_3(CH_2)_{16}COOH$ | Stearic Acid |
| $CH_3(CH_2)_3CH=CH(CH_2)_7COOH$ | Myristoleic acid |
| $CH_3(CH_2)_5CH=CH(CH_2)_7COOH$ | Palmitoleic acid |
| $CH_3(CH_2)_8CH=CH(CH_2)_4COOH$ | Sapienic acid |
| $CH_3(CH_2)_7CH=CH(CH_2)_7COOH$ | Oleic acid |
| $CH_3CH_2CH=CHCH_2CH=CHCH_2CH=CH(CH_2)_7COOH$ | α-Linolenic acid |

Representative of monocarboxylic aromatic acids are:

| | | |
|---|---|---|
| $C_6H_4(COOH)_2$ | [benzene-1,2-dicarboxylic acid] o-phthalic acid | o-phthalic acid |
| $C_6H_4(COOH)_2$ | [benzene-1,3-dicarboxylic acid] | isophthalic acid or m-phthalic acid |
| $C_6H_4(COOH)_2$ | [benzene-1,4-dicarboxylic acid] | terephthalic acid or p-phthalic acid |
| o-$HOC_6H_4COOH$ | [o-hydroxybenzoic acid] | salicylic acid |
| o-$CHOOC_6H_4COOH$ | [o-acetylsalicylic acid] | aspirin |

Representative of dicarboxylic saturated and unsaturated acids are:

| | |
|---|---|
| HOOC—COOH | Oxalic acid |
| HOOC—$(CH_2)$—COOH | Malonic acid |
| HOOC—$(CH_2)_2$—COOH | Succinic acid |
| HOOC—$(CH_2)_3$—COOH | Glutaric acid |
| HOOC—$(CH_2)_4$—COOH | Adipic acid |
| HOOC—$(CH_2)_5$—COOH | Pimelic acid |
| HOOC—$(CH_2)_6$—COOH | Suberic acid |
| HOOC—$(CH_2)_7$—COOH | Azelaic acid |
| HOOC—$(CH_2)_8$—COOH | Sebacic acid |
| $HO_2CCH=CHCO_2H$ | Maleic acid (cis form) Fumaric acid (trans form) |
| $HO_2CCH=CHCH_2CO_2H$ | Glutaconic acid |
| $HO_2C(CH_2)_8CH=CHCO_2H$ | Traumatic acid |

Representative of tricarboxylic acids are:

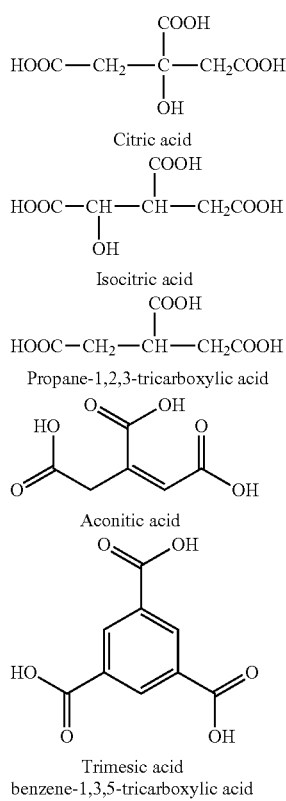

The ratio of trona to carboxylic acid may vary on a w/w basis. Although other ratios may be useful, as a general guideline, the ratio can often range from 200:1 to 5:1, and in some cases can be from 30:0.5 to 5:1. For example, in the case of citric acid, ratios of about 9:1 are particularly preferred. The ratio can depend on the particular carboxylic acid, the number of acid groups and other functional groups, the molecular weight and other factors that can be determined systematically.

The amount of trona/carboxylic acid will generally be contained in a pouch or packet that is permeable to oxygen or oxygen and water or other liquid depending upon the intended use. Packets can contain measured weight amounts of this mixture ranging from 0.1 to 50 grams per packet to be used to treat 50 to 500 cubic feet of air surrounding the oxygen perishable goods being treated or protected. When used in a liquid environment, such as the cooling of cooked meat segments in a water reservoir the trona/carboxylic acid packets may also contain from 0.1 to 50 grams, in single or multiple packets and used to treat up to 500 gallons of water. Preliminary tests have shown two packets containing about 36 grams each of a 9:1 (w/w) trona/citric acid mixture is sufficient to treat 450 gallons of water in order to reduce the temperature of 900 lbs beef shanks cooked to a temperature of about 150° F. to a marketable temperature in about half the time it took to cool similar shanks cooled only by being immersed in water at the same initial temperature.

The trona and carboxylic acid can often be provided in a dry particulate form. Although particle size can vary, sizes from about 0.01 mm to about 5 mm can be useful, and in many cases ranges from about 0.05 mm to about 1.5 mm. Particle size can affect exposed surface area of the dry mixture and rates of oxygen uptake. Additional materials can optionally be added to the trona/carboxylic acid mixture such as, but not limited to, stabilizers, colorants, fillers, and the like.

The trona and carboxylic acid compositions can often be enveloped in a packet which holds a predetermined amount of the composition within a packet volume. The packet can be formed to allow oxygen and air to permeate from surrounding environment into the packet volume to contact the oxygen capturing composition. Packet sides and walls can be perforated or be formed of porous material. Alternatively, a non-porous material can be used which is then opened immediately prior to use. For example, packets can be formed of plastic film, perforated plastic film, fabric, paper, or the like. Non-limiting examples of suitable materials include polyester films, polyester terephthalate (PET) films, paper, and the like. The packets can range in size depending on the application, and often range in dimensions of about 1 $cm^2$ to 100 $cm^2$.

Packets may be replaced as necessary. Generally, spent or used packets can be determined by noting a rise in temperature within the monitored environment, oxygen sensors, or other similar approaches. Optionally, one or more packets can be sealed in a transport package which isolates the packet(s) from exposure to oxygen until ready for use.

The invention also relates to methods for using packets of the combined trona and mono-, di- and tri-carboxylic acids compositions to absorb oxygen from and prolong the useable life of a variety of perishable products, which may include foods, fresh vegetables and fruits, grains and other plant products, animal products and the like. Although not required, performance of the compositions can often be increased in moist or humid environments. For instance, a moist or humid atmosphere can be obtained by humidifying or spraying with water vegetables, fruits or other produce in grocery stores, restaurants, refrigerated trucks, or other locations, where packets containing the trona/acids compositions are strategically placed thereby maintaining the freshness of the produce for a period longer than is otherwise possible.

Another method for applying the aqueous composition is to immerse a perishable product within a water bath or other aqueous environment. For example, freshly cooked meat under USDA guidelines requires a drop in temperature from cooking temperature, i.e. ~145° C. to ~45° in six hours or less. Upon the trona/carboxylic acid coming into contact with water and endothermic reaction is produced and the temperature within the immediate surrounding environment is lowered.

Still another method according to the implementations of the invention, the trona and di- or tri-carboxylic acid combination can be formulated as a dry mixture and packaged in moisture absorbent devices such as moisture permeable packets of various sizes that encase the combined materials. These packets can be strategically placed is vicinities appropriate to contact with the perishable products when moisture is present. For example, the such packets may be constructed and used to introduce carbon dioxide into and absorb oxygen from produce bins, produce loaded into trucks, railway cars and ships, refrigerators, frozen food lockers, butchered meat storage lockers and directly to produce to extend the useable life or shelf life of produce beyond what has been previously possible. The invention can also be used to prevent exposed, refrigerated meats, fish, seafood, cheeses, and other similar foods from prematurely discoloring and spoiling. The shelf life of cookies, breads, cakes, brown sugar, tortillas, and other dry or non-refrigerated foods can also be extended according to the present invention. When used in transportation or storage in bins, crates, or the like the transportation means, trucks, train cars, ships etc. will be refrigerated. The same holds true for display in grocery stores, stands, or other display units where ambient temperatures would hasten product degradation. Further, packets of trona and carboxylic acids may be placed in perforated pipes or other ventilating devices that release carbon dioxide and absorb oxygen when activated by moisture. Once it has been determined how many packets of trona and carboxylic acid are required for any enclosed environment they can be place in any desired space and packet size relative to the material to be treated. It is advantageous that this material is non-toxic, releases carbon dioxide and, in some manner not fully understood also absorbs oxygen.

While not known for a certainty, as previously noted, it appears plausible that the atoms of an adsorbed gas, such as oxygen, are in direct chemical combination with the atoms in the surface of the solid trona carboxylic acid mixture or combinations. These surface oxygen atoms, by reason of their position, may be in a chemical state which is somewhat different from that of the atoms within the body of the solid trona/carboxylic acid combination. The oxygen atoms adsorbed on the surface of the trona and/or carboxylic acid mixture may, therefore, be considered as chemically combined, and their chemical environment is not essentially different from that of the oxygen atoms just within the bonding "surface" of the trona carboxylic acids combination itself. It is believed that it is the trona that provides the surface for the oxygen absorption and not the di- or tri-carboxylic acid but ongoing tests are being conducted to verify this belief. What is known is that it functions in the uptake of oxygen as will be demonstrated below As in the preceding paragraph, it is not known for a certainty how the solid trona carboxylic acid mixture or combinations serve as an oxygen absorber. The interaction of the carbonates or bicarbonates in trona, reacting with the carboxylic acid certainly function, at least in part, as an acid and base releasing carbon dioxide and water. However, there are additional reactions or interactions that take place when trona, a carboxylic acid and optionally moisture come together that are unexplained in that, oxygen, in addition to that present in the carbonates, is taken up such that the oxygen in the surrounding atmosphere is reduced or minimized.

The term oxygen uptake composition is used over terms oxygen absorber or oxygen adsorber. Various theories may be postulated but what is known through repeated demonstrations is that the combination of trona and carboxylic acids within the confines as described herein, and optionally in the presence of moisture, will reduce, minimize or eliminate the presence of oxygen in the immediate atmosphere surrounding oxygen perishable goods.

Application of moisture to strategically placed packets of powdered trona and carboxylic acids can be accomplished by the introduction of an aqueous spray or fogging in of mist into the enclosure containing the packets and perishable product to be treated. For enclosed structures such as display cases, crates, trucks, railway cars, ships, refrigerated containers for meats and other food products, and the like this can be readily accomplished. One distinct advantage of the trona carboxylic acid mixture is that it produces an endothermic reaction in addition to providing carbon dioxide and absorbing oxygen and therefore has an additional cooling effect.

When the combined cooling and oxygen absorption effect of items in bunched or clumped form is required, such as the cooling of large pieces of cooked meat is required, the trona/carboxylic acid composition of the invention can also be contained in a water and gas permeable packaged form which is added to a water container holding the meat to be cooled. Chunks of ice plus the endothermic action of the trona carboxylic acid packets in the container accelerates the cooling time. Monitoring the temperature drop and adding additional packets of trona carboxylic acid packets and ice makes it possible to reduce the cooling time of such cooked meat from the required six hours to less than three hours. As used herein "meat" may be inclusive of flesh from all forms of animal life, preferably used for human consumption. Animal life is broadly deemed to be inclusive of four-legged animals such as cattle, sheep, swine, deer, elk, moose and the like which are slaughtered and used or preserved for human consumption. Animals are also inclusive of birds of all kinds and primarily those used for human consumption and lake, stream or sea life including fish, shell fish and the like.

Oxygen perishable products per se are not limited to any specific category of class so long as such product is perishable in the presence of oxygen and can be passivated or preserved by an oxygen uptake composition and in the presence of carbon dioxide, preferably under refrigerated conditions. Therefore, any product or item such as those mentioned above including products from plants and animals are inclusive and are exemplified by fruits, vegetables, grains, meats, dairy products, processed fruits, and any of the above which have been processed and/or combined into mixtures such as casseroles, soups, baked goods, or any other processed form fit within the definition of oxygen perishable goods. In addition to oxygen perishable goods, it may also be possible to utilize the trona/carboxylic acid compositions to stabilize or extend shelf life of oxygen scavenging or absorbing chemicals such as functioning as an anti-caking agent.

Applying the trona carboxylic acid packets in the environment of perishable products also has significant advantages over conventional humidifying devices. The absorption devices are self-contained units that do not require electrical power or other external energy sources. Accordingly, the packets described herein can be used in many environments where conventional humidifying devices have been impractical or impossible. The cost of manufacturing and operating the packets disclosed herein are less than those associated with conventional humidifying systems, due to the simple design of the packets, their lack of moving parts, and their ability to operate without electricity. Other advantages of using the trona carboxylic acid packets disclosed herein, include portability, reusability of the packets in different locations, and ease of use.

FIG. 1 is a perspective view of a liquid or gas permeable woven packet 100 having a front 105 a back (not shown) and sealed at the perimeters 101, 102, 103 and 104 enveloping a particulate mixture 106 of trona and and one or more mono-, di- or tri-carboxylic acids.

Figure 2:
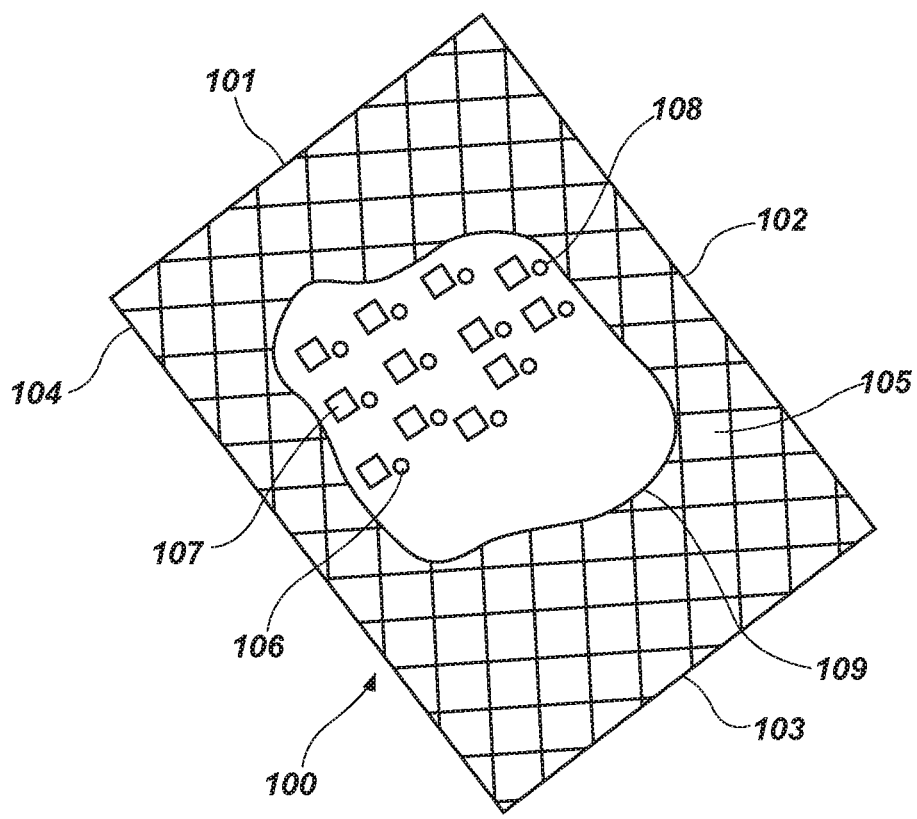
FIG. 2 is a partial breakaway view of the packet of FIG. 1 showing the trona and carboxylic acid particles in the interior of the packet.

FIG. 2 is a perspective view of the packet 100 as shown in FIG. 2 with a cut away—109 in the front 105 exposing the particulate mixture 106 consisting of particles of trona 107 and a mono-, di- or tricarboxylic acid 108.

Figure 3:
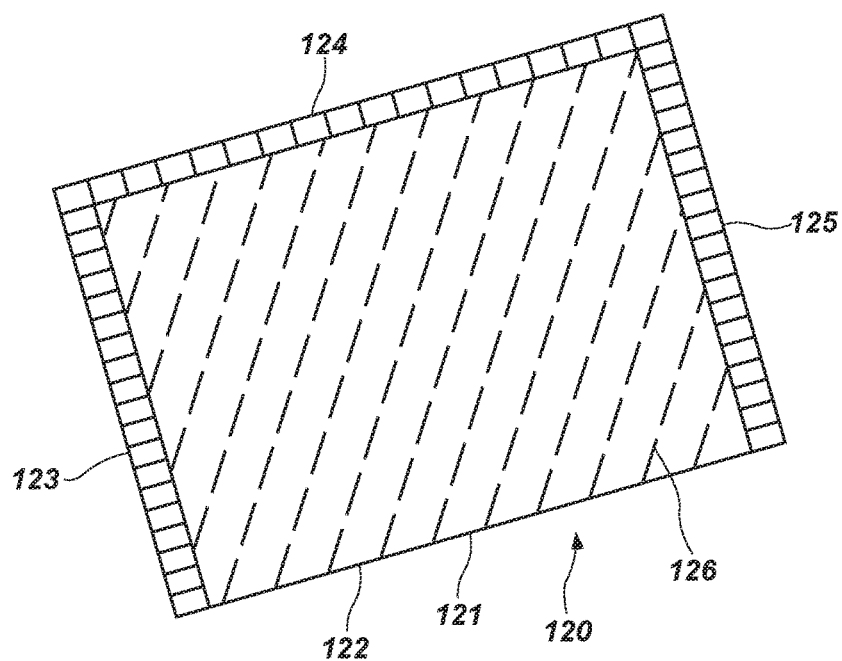
FIG. 3 is a perspective view of a gas permeable package of the invention containing a mixture of trona and one or more mono-, di- or tri-carboxylic acids.

FIG. 3 is a perspective view of a gas permeable only folded plastic packet 120 having a front 121 a back (not shown) and sealed at the perimeters 123, 124, and 125 enveloping a particulate mixture of trona and one or more mono-, di- or tri-carboxylic acids (not shown). Optional perforations 126 can be formed in the plastic film of the packet 120 to allow gases to permeate into and out of the packet. The plastic packet can be formed of any suitable material such as plastic film, rigid plastic, porous fabric, and the like. Non-limiting examples of suitable packet material can include polyethylene film, woven or non-woven fabric, cloth, and the like. The perforations can be patterned along lines, along a grid, or oriented random positions across one or more surfaces of the packet.

Figure 4:
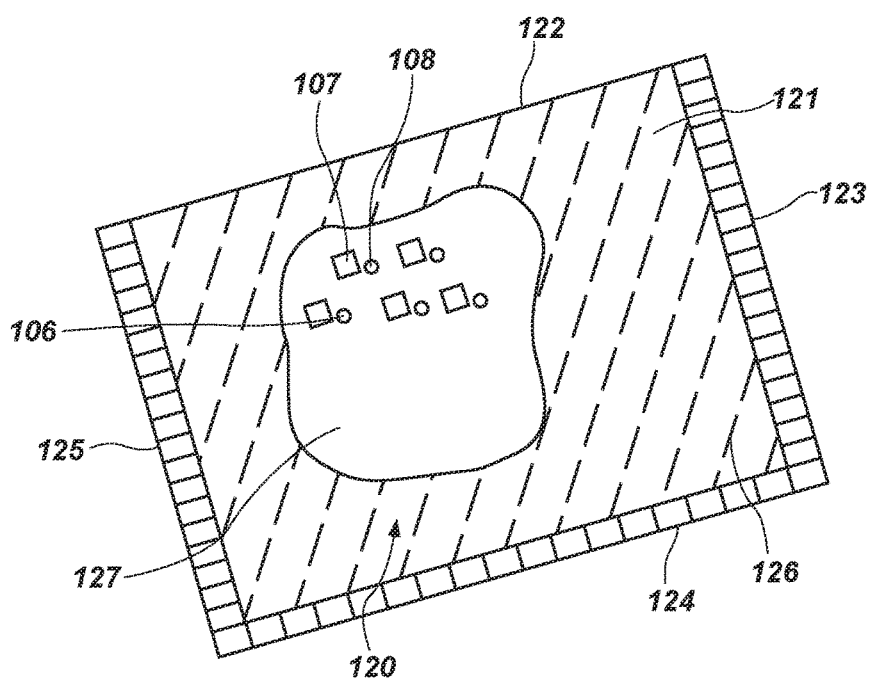
FIG. 4 is a partial breakaway view of the packet of FIG. 3 showing the trona and carboxylic acid particles in the interior of the packet.

FIG. 4 is a perspective view of the packet 120 as shown in FIG. 3 with a cut away 127 in the front 121 exposing the particulate mixture 106 consisting of particles of trona 107 and a mono-, di- or tricarboxylic acid 108. The packet can optionally be folded along fold 122.

Figure 5:
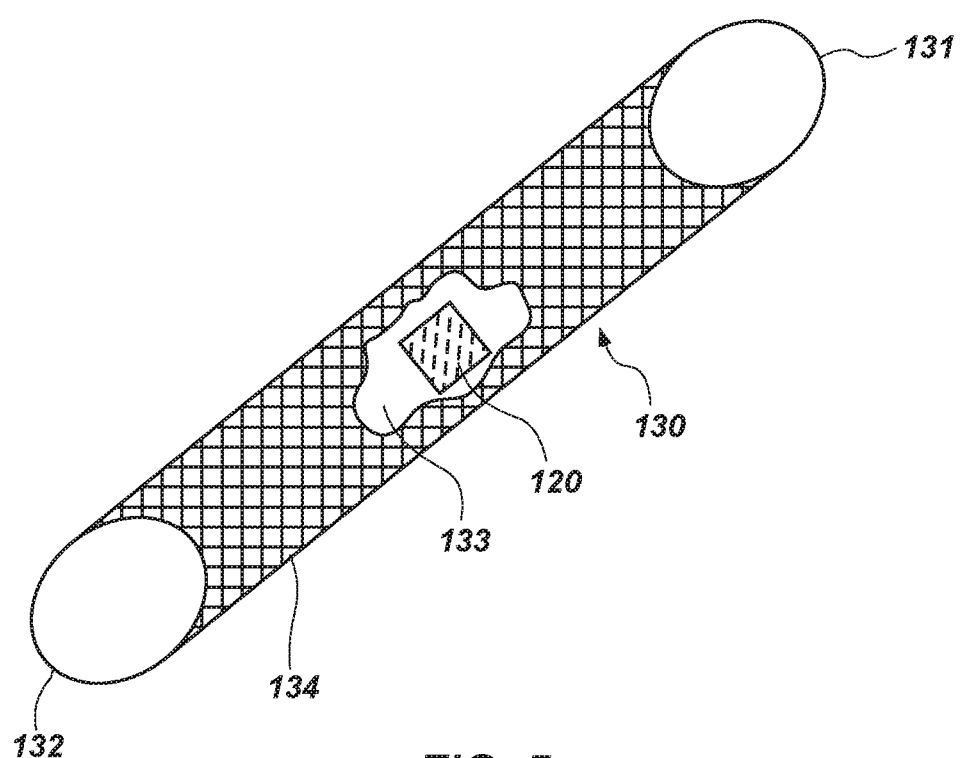
FIG. 5 is a perspective view of a gas permeable tube containing, in partial breakaway, a packet as shown in FIG. 3.

FIG. 5 is a perspective view of an elongated gas permeable tube 130 having open ends 131 and 132 and containing in partial breakaway 133, at least one gas permeable packet 120 containing, in granular form, trona and a mono-, di- or tricarboxylic acid mixture 106 as shown in FIG. 1. Tube 130 can be formed of a material which is aperture such as a metal mesh 134, grid, perforated sheet, or the like.

Figure 6:
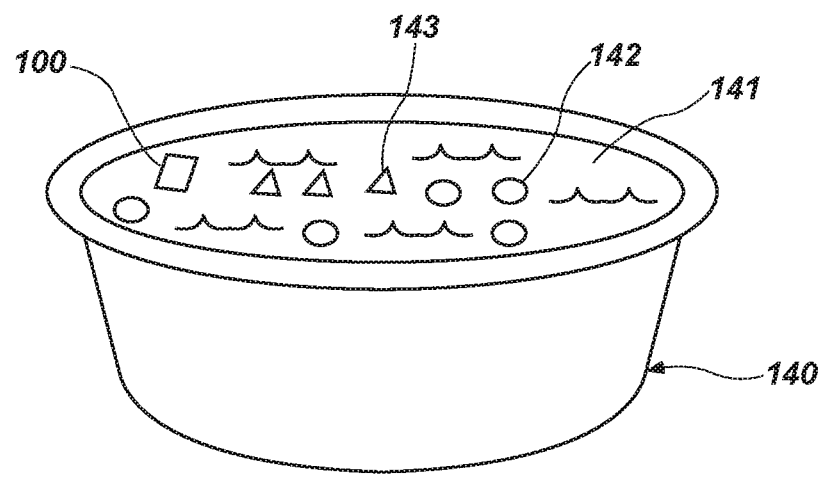
FIG. 6 is a perspective view of a liquid container for holding pieces of oxygen perishable goods, pieces of ice and packets of gas and liquid permeable packets as shown in FIG. 1.

FIG. 6 is a perspective view of a liquid container 140 filled with water 141 holding segments of oxygen perishable goods 142, such as chunks of cooked meat, in need of rapid cooling, pieces of ice 143 and one or more liquid and gas permeable packets 100 as shown in FIG. 1 enveloping a particulate mixture 106 of trona 107 and one or more mono-, di- or tri-carboxylic acids 108.

Figure 7:
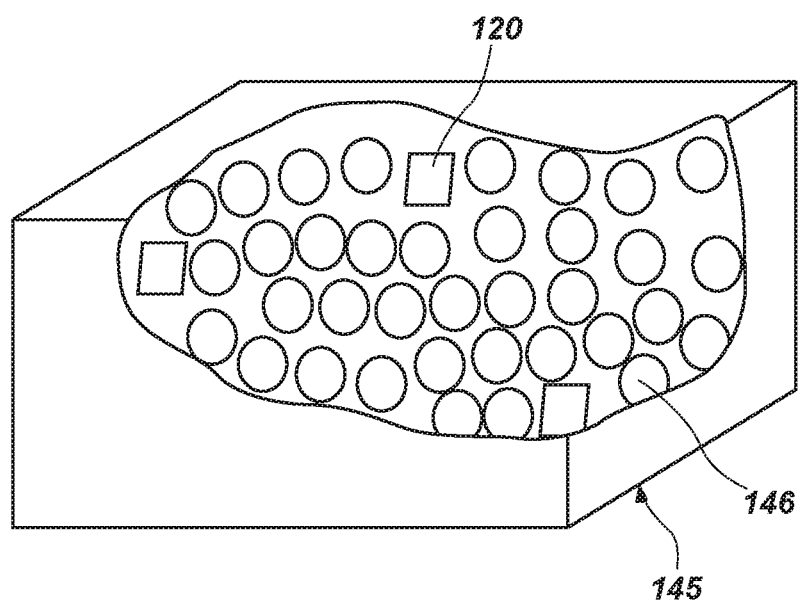
FIG. 7 is a perspective view of a container or crate holding oxygen perishable goods for shipment and also containing one or more packets as shown in FIG. 3.

FIG. 7 is a cut away view of an enclosed shipping crate 145 containing oxygen perishable fruit 146 and having gas permeable packets 120 of the trona carboxylic acid mixture 106 distributed throughout the crate 145 as needed to adsorb/absorb oxygen and produce an atmosphere of carbon dioxide surrounding the fruit.

Figure 8:
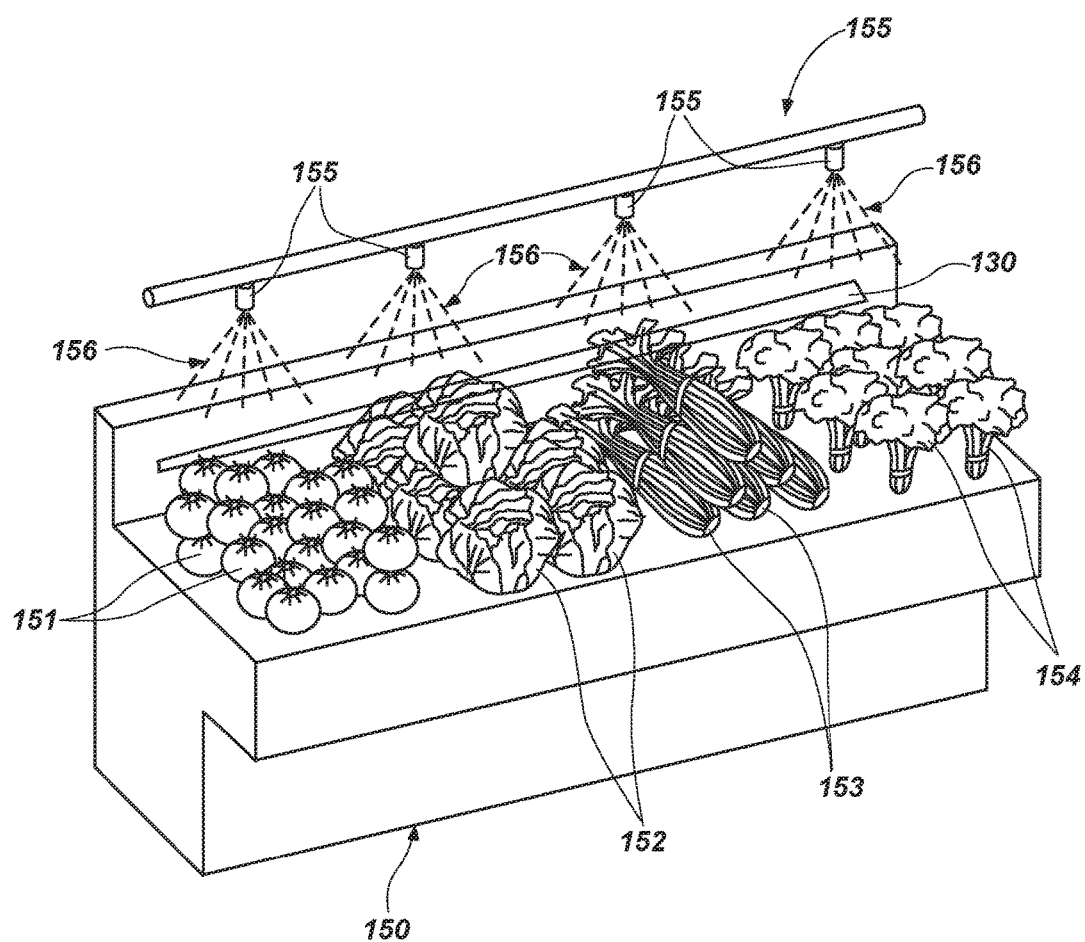
FIG. 8 is a perspective view of a display stand holding oxygen perishable goods adapted for water spray means and showing packets of FIG. 3 strategically placed.

FIG. 8 is a perspective view of a produce display 150 containing oxygen degradable produce such as tomatoes 151, lettuce 152, celery 153 and broccoli 154 and retained in a moist environment by mean of an aqueous spray 156 fed through a supply line to spray nozzles 156. Also in the moisture containing environment is a gas permeable elongated tube 130, as shown in FIG. 5, containing strategically located gas permeable packets of granulated trona and a mono-, di- or tri-carboxylic acid (not shown) to absorb/ adsorb oxygen form the immediate environment and enhance a presence of carbon dioxide.

Figure 9:
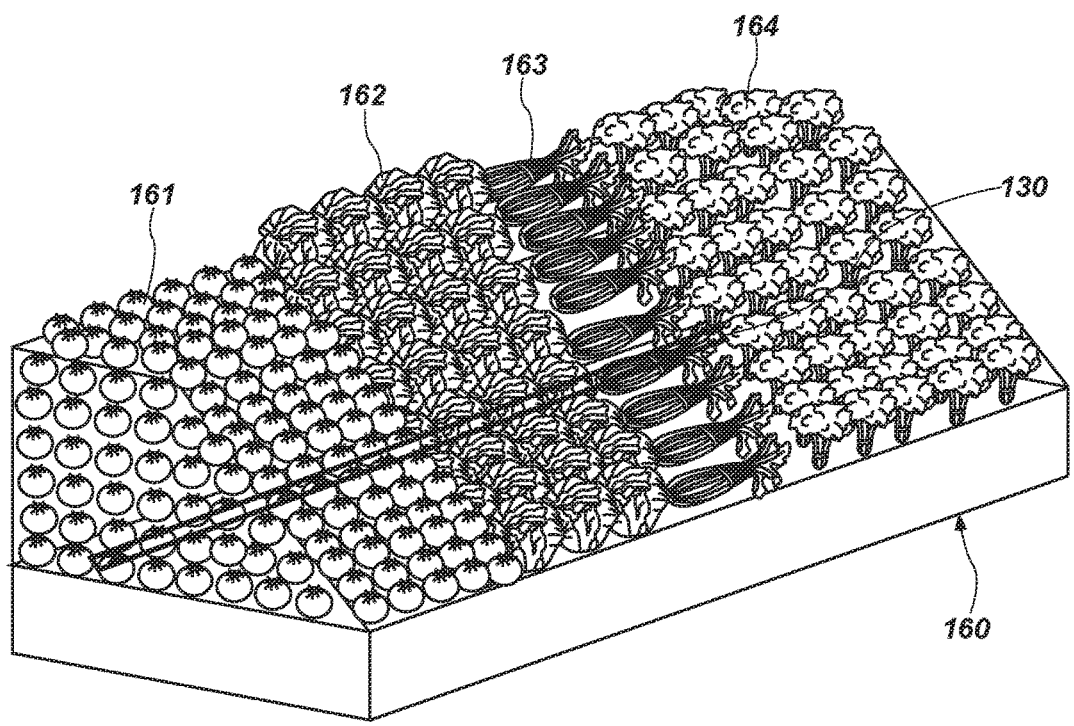
FIG. 9 is a perspective view of a refrigerated display case containing oxygen perishable goods and containing a gas permeable tube containing trona/carboxylic acid packets as shown in FIG. 5.

FIG. 9 is a perspective view of yet another enclosed refrigerated display container 160 showing oxygen perishable deli vegetables such as olives 161, cauliflower tips 162, carrot sticks 163, and mushrooms 164 and having inserted into the interior environment of the container an elongated gas permeable tube 130 as shown in FIG. 5 containing in one or more gas permeable packets (not shown) containing, in granular form, trona and a mono-, di- or tricarboxylic acid mixture as shown in FIG. 3.

Figure 10:
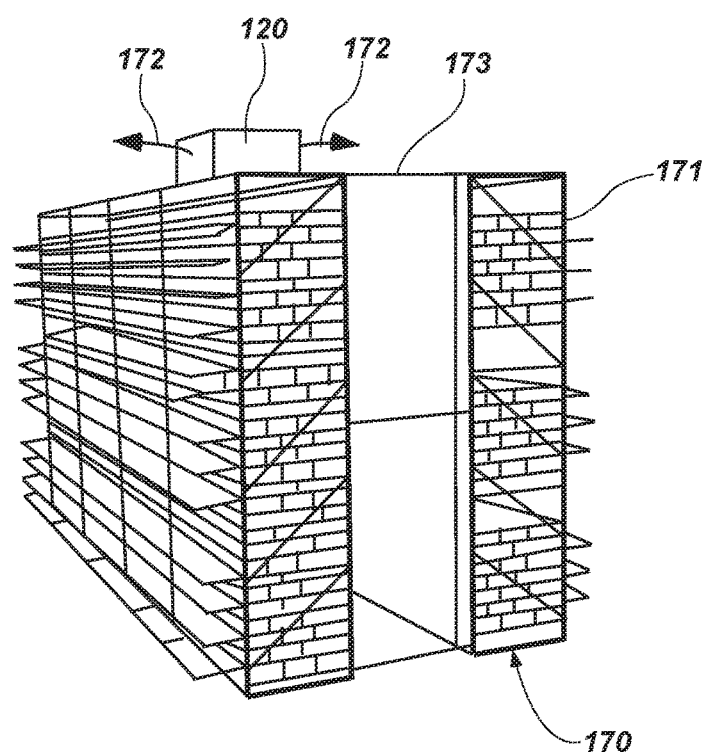
FIG. 10 is a representation of a storage unit showing shelving, air flow arrows, oxygen absorber packet storage for placing in a warehouse or other storage areas.

FIG. 10 is a perspective view of a warehouse storage unit 170 containing shelving 171 and ventilated throughout as shown by directional arrows 172 and 173. The warehouse is maintained in a moisture or humidity controlled environment for the storage of oxygen perishable goods 173. Packets of trona and carboxylic acid as shown in FIG. 3 may be strategically placed on the shelving 171 to absorb/adsorb oxygen from environment surrounding the perishable goods 173 and replace it with a carbon dioxide environment.

Figure 11:
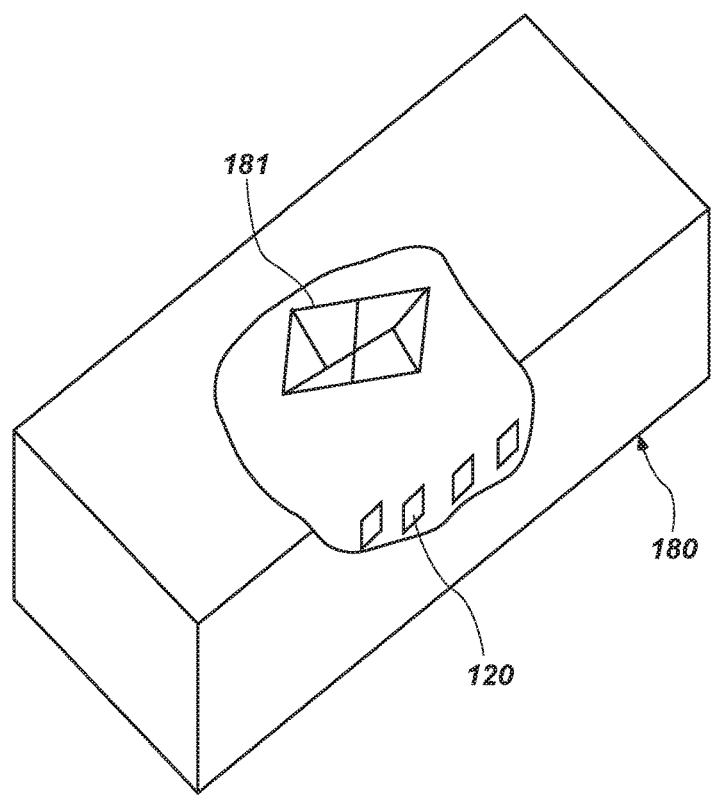
FIG. 11 is a partial breakaway view of a cargo shipping container having placed therein containers or crates filled with oxygen perishable goods such as shown in FIG. 7 for shipment in trucks, railway cars, cargo ships, and as air freight.

FIG. 11 is a partially cut away view of a shipping container 180 for transporting prepackaged oxygen perishable goods represented by 181. Goods 181 may be enclosed in containers or crates which may be sealed or in slatted type crates to promote air circulation. The container 180 and prepackaged goods 181 within may be loaded as cargo on a train, truck, ship, airplane or other means of transportation. Packaged within the goods 181 or in container 180 may be placed any number of trona/acid packets 120 based on the projected oxygen absorption/adsorption from within the environment of the goods and also bringing about an enhanced presence of carbon dioxide within the environment of the oxygen perishable goods. The moisture present within the cargo space or hold during shipping and the determination of how much trona/acid should be present and the size of the packets containing the same can be determined by one skilled in the art depending on numerous factors, distance of shipping, humidity of the outside environment, volume of perishable goods being transported, size of the containers, etc.

Figure 12:
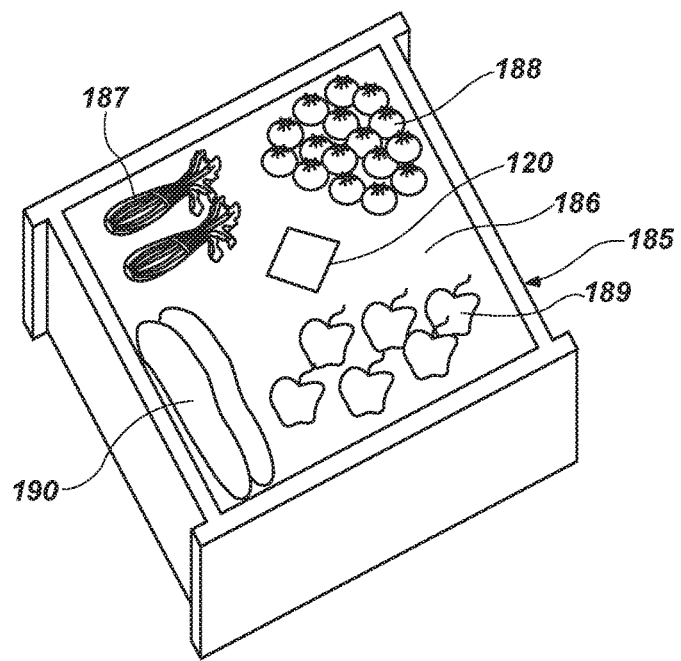
FIG. 12 is a perspective view of a container having either no lid or a clear lid and holding oxygen perishable goods for display or shipment and containing gas permeable packets of trona/carboxylic acid to adsorb/absorb oxygen and produce carbon dioxide.

FIG. 12 is a perspective view of a display or shipping container 185 having a transparent or open top 186 and filled with oxygen perishable produce such as asparagus 187, grapes 188, apples 189 and cucumbers 190, preferably stored in a humidity controlled environment and containing gas permeable packets 120 of trona/carboxylic acid mixtures as shown in FIGS. 3 and 4 wherein the trona/carboxylic acid mixtures are activated by the presence of moisture within the container and the surrounding environment to absorb/adsorb oxygen and enhance the presence of carbon dioxide.

Figure 13:
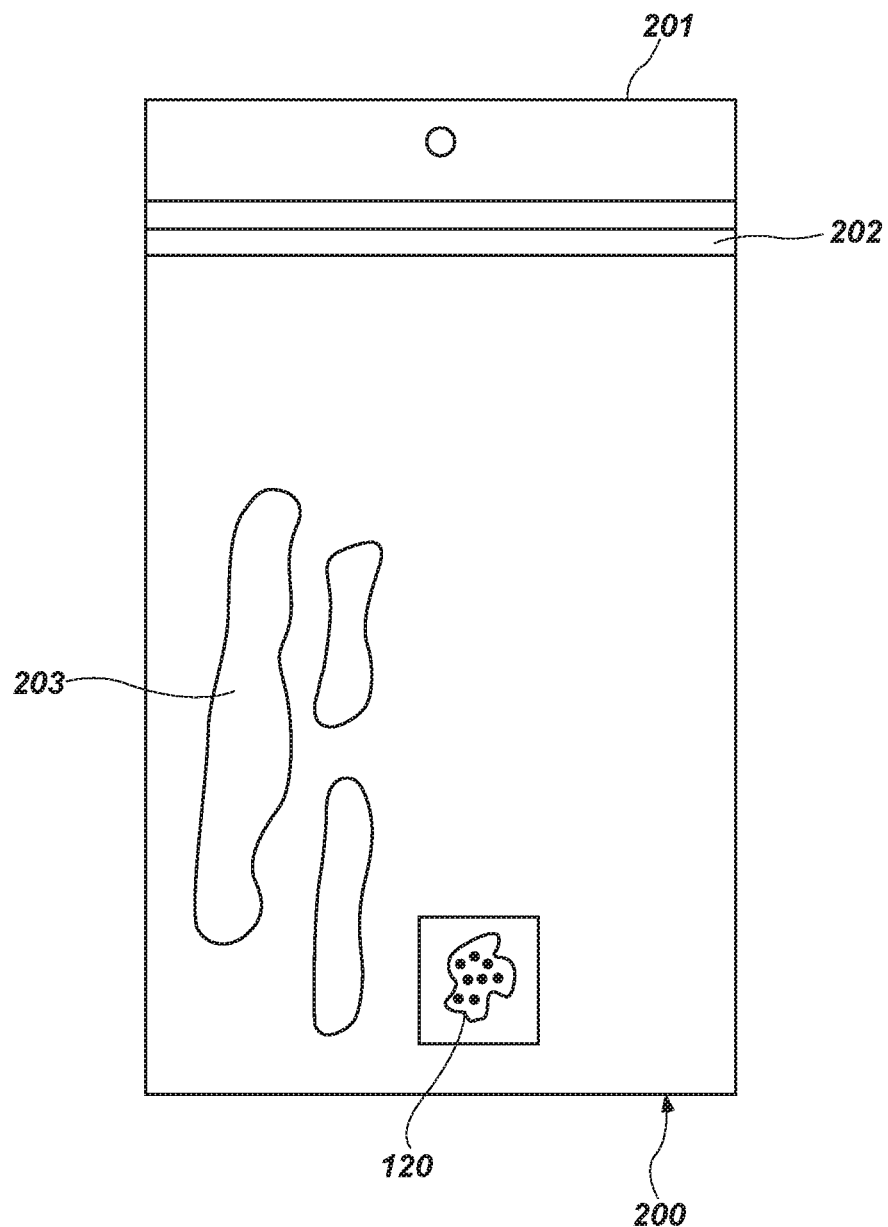
FIG. 13 is a view of a plastic reclosable bag marketing jerky strips and containing gas permeable trona/carboxylic acid packet(s).

FIG. 13 is a front view of a reclosable plastic envelope or bag 200 that can be resealed at the top 201 by a zipper type action 202. Inserted into the bag 200 are strips of jerky 203 or other oxygen perishable produce having limited moisture content. Also contained within the bag are gas permeable packets 120 of a granular mixture of trona and mono-, di- or tri-carboxylic acids such as shown in FIGS. 3 and 4. The trona/carboxylic acid mixture is designed to lessen the oxygen content and result in an increase in carbon dioxide in the bag interior. The amount of trona/carboxylic acid is determined so as not to dehydrate the jerky strips such that they become friable. In other words a minimal amount of moisture is to be tolerated in the jerky strips. However, the carbon dioxide content is sufficient to prevent the strips from being contaminated by bacteria, mold, etc. Even with repeated opening and closing of the bag, the jerky remains free of such contamination. Similar envelopes or bags can be used to store and preserve a wide variety of dehydrated foods such as, but not limited to, fruits, vegetables, nuts, snacks, and the like.

Figure 14:
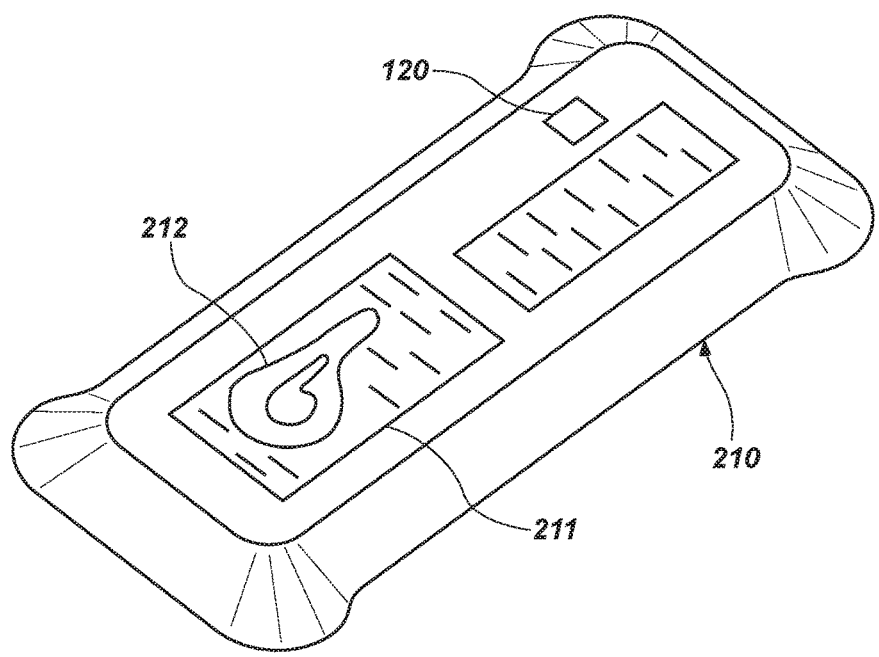
FIG. 14 is a view of a tray for marketing fresh meat products placed on absorbent pads for absorbing liquids and also containing gas permeable packets of trona/carboxylic acid placed on the tray.

FIG. 14 is a perspective view of a tray 210 or similar type container having placed thereon absorbed pads 211 on which oxygen degradable produce such as fresh meat 212 can be placed. Exemplary of fresh meat 212 is beef, pork, fish and poultry. Illustrated at the meat in FIG. 14 is a beef steak. The moisture from the steak will be absorbed by the pads 211. Also on the tray are one or more gas permeable packets 120 of a granular mixture of trona and mono-, di- or tri-carboxylic acids such as shown in FIGS. 3 and 4. The tray 210 may be placed in an enclosed display case (not shown) where oxygen in the environment surrounding the meat is adsorbed/absorbed by the trona/carboxylic acid mixture in the packets 120 thereby lessening the oxygen content in this atmosphere and also resulting in an increase in carbon dioxide in the surrounding environment.

Figure 15:
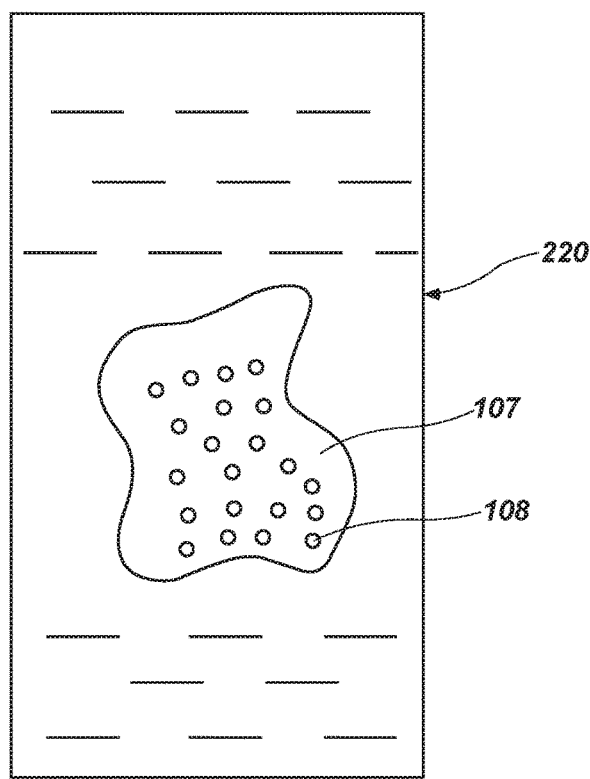
FIG. 15 is a view of an absorbent pad for displaying fresh meat products and absorbing liquids, such a blood, and, in a partial breakaway view, showing granules of trona and mono-, di- or tricarboxylic embedded in the pad.

FIG. 15 is a top plan view of a gaseous and moisture absorbent pad 220 for holding meat or other oxygen perishable produce in an enclosed environment (not shown). In partial break away is shown a granular mixture of trona 107 and mono-, di- or tri-carboxylic acids particles 108 embedded in this pad 220 for absorbing/adsorbing oxygen from the environment surrounding the pad 220 thereby lessening the oxygen content and also resulting in an increase in carbon dioxide in such environment.

Figure 16:
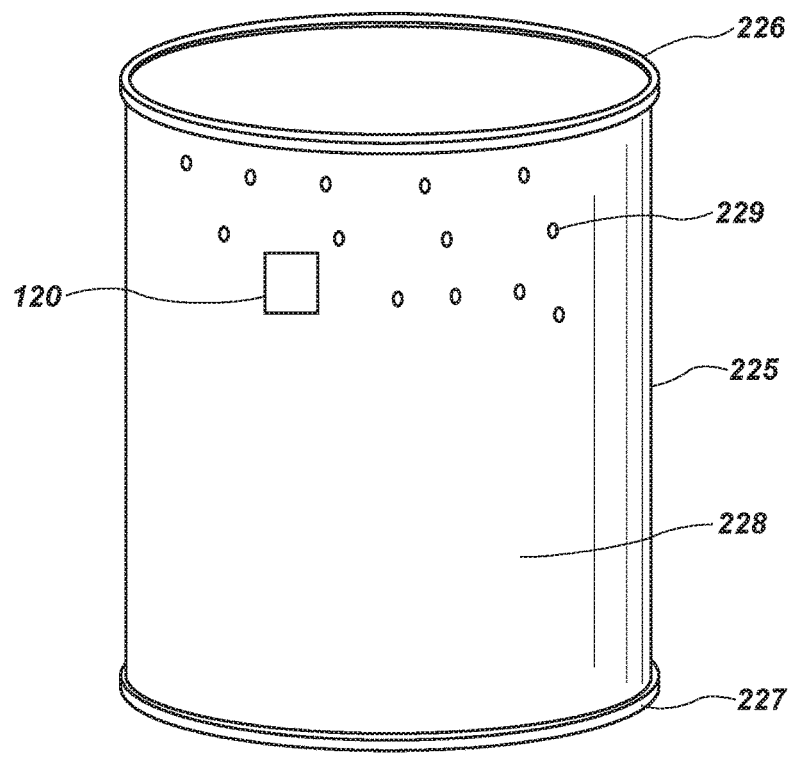
FIG. 16 illustrates a sealed No. 10 can for holding grain kernels or other particulate matter and also containing packets of trona/carboxylic acid for absorbing/adsorbing oxygen and forming a carbon dioxide atmosphere within the can.

FIG. 16 is a perspective view of a round storage can or container 225, such as a No. 10 can, having a closable top or lid 226 and a sealed bottom 227. The interior 228 of the container may contain oxygen degradable grain kernels 229 such as corn, wheat, barley, rice, and the like, and also gaseous permeable packets 120 of a granular mixture of trona and mono-, di- or tri-carboxylic acids. The container 225 may be opened and closed as warranted and some of the grain kernels 229 removed. Oxygen in the gaseous space within the container 225 is adsorbed/absorbed by the granular mixture of trona and carboxylic acid which prevents spoilage from occurring. Carbon dioxide formed within the container prevents oxidation of the grain kernals and spoilage from occurring.

Figure 17:
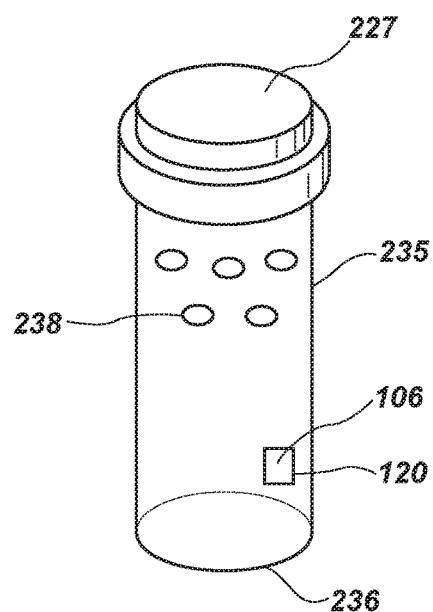
FIG. 17 illustrates a bottle with a replaceable cap containing pharmaceutical tablets or capsules and also a packet of trona/carboxylic acid to absorb/adsorb oxygen and promote the formation of carbon dioxide within the bottle.

FIG. 17 is a perspective view of a see through storage container 235 having a sealed bottom 236 and a closable top 237 for holding dosage units of medication 238 such as pills, tablets, capsules, lozenges, and the like. Within the container 235 in addition to the medication 238 is a gas permeable packet or packets 120 of a granular mixture 106 of trona and mono-, di- or tri-carboxylic acid particles for absorbing/ adsorbing oxygen from the environment within the container and surrounding the medication. The container 235 may be opened and closed repeatedly by removing the top 227 to remove units of medication 238 thereby allowing for the entrance of oxygen containing outside air. Even with repeated opening and closing, the oxygen within the interior of the container 235 will be absorbed by the trona/carboxylic acid granules for an extended period of time and the carbon dioxide content within the container will be enhanced preventing the medication from being oxidized and degraded.

In yet another optional application, the granular mixture can be used while microwaving foods. For example, the granular mixture or a packet of the granular mixture can be included within a microwave chamber during heating of food. The granular mixture is substantially free of iron or other materials which would cause sparking or bursting. Thus, packets of the granular mixture can be associated with pre-packaged foods and do not need to be removed by customers upon heating of the food.

Figure 18:
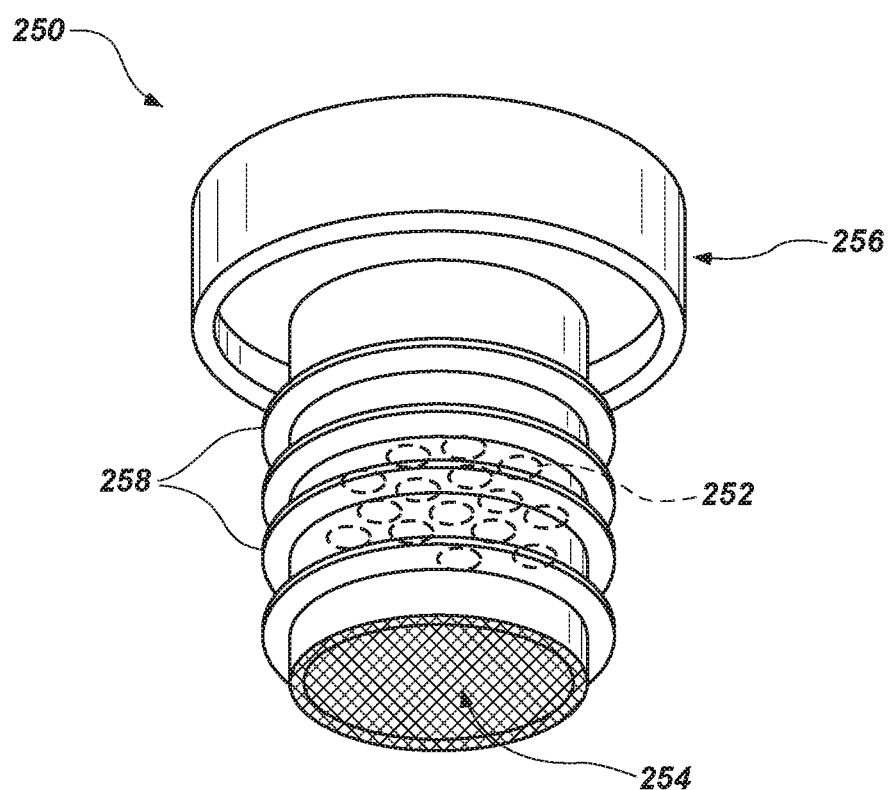
FIG. 18 illustrates a beverage stopper having the granular mixture contained therein for preserving freshness of a beverage.

FIG. 18 is a perspective view of a beverage stopper 250 having the granular mixture 252 oriented within a chamber 254 of the beverage stopper. The beverage stopper can be shaped to fit within an opening of a wine bottle, carbonated beverage, cooler, beer, or any other beverage container. The stopper can include a top portion 256 which prevents gases from escaping or entering the beverage and a chamber which is fluidly associated with an interior of the beverage container. Optional flexible spaced flanges 258 can be engageable with inside edges of a throat of the beverage container. The chamber can also include a mesh or perforated edge which retains the granular mixture within the chamber while also allowing gases and liquids to pass into the chamber. Presence of the granular mixture allows for maintaining freshness of the beverage after opening from a hermetically sealed condition for an extended period of time. Although conditions can vary, freshness of wines, for example, can be extended from a couple of days to over a week or more.

EXAMPLES

Example 1

This Example Demonstrates Oxygen Absorption with Trona/Citric Acid Mixtures

In order to test the oxygen removing capacity of the present invention, an oxygen permeable packet containing trona with citric acid powder, at a weight ratio of 9:1, was placed in a one inch diameter by three inch long test tube. In an identical tube a one-gram sample of a commercial iron/iron oxide powder, also in an oxygen permeable packet, was tested to compare the oxygen absorbing results of the present invention to a product that is presently used commercially. These tubes were sealed for 20 minutes after the introduction of the packets. A gas chromatograph-mass spectrometer (GC-MS) was used to analyze the oxygen content of the air in the tube. Ambient air contains greater than 200,000 ppm (parts per million) by weight oxygen. After twenty minutes exposure of the air in the respective tubes, the tube containing the trona/citric acid sample registered 11.06 ppm of oxygen and tube containing the iron/iron oxide sample registered 15.85 ppm oxygen. The caps were removed and the tubes were exposed to ambient air for 30 minutes with the respective samples remaining in the tubes. The tubes were then sealed for another 20 minutes and the air in the tubes was again analyzed for oxygen using a GC-MS. The trona/citric acid tube registered 8.96 ppm oxygen and the iron/iron oxide tube registered 15.23 ppm oxygen. Interestingly, the second test showed better oxygen removal results than the first test particularly for the trona/ citric acid. Presumably this is due to the trona/citric acid sample in the tube continuing to absorb oxygen even while the tube was open to the atmosphere These tests demonstrate that the trona/citric acid packet absorbed oxygen significantly better than the iron/iron oxide packet.

Example 2

This Example Confirms the Results of Example 1

It was calculated that 11.6 mg of the trona/citric acid product of Example 1 would be comparable, on a w/v basis, to a two gram packet of the same product in a #10 tin can used for food storage. To further compare the oxygen removing capacity of the present invention with the commercial oxygen absorbing iron/iron oxide product, 11.6 mg of each of these products, in a sealed oxygen permeable packet, were placed in a one inch by three inch tube as in Example 1. When the 11.6 mg trona/citric acid packet was placed in the tube and analyzed after the tube was sealed for 20 minutes as in Example 1, the GC-MS analysis showed the oxygen content in the tube had been lowered to 43.7 ppm. When the 11.6 mg of iron/iron oxide packet was sealed in the tube for 20 minutes, it had reduced the oxygen content to 43.1 ppm. As in Example 1, these tubes were exposed to air for 30 minutes and after the tubes were again sealed for 20 minutes, the trona/citric acid tube contained 35.8 ppm oxygen and the iron/iron oxide tube contained 40.2 ppm oxygen. These tests again demonstrate that the present invention of trona/citric acid removed oxygen as well as, or better than, the commercially used iron/iron oxide oxygen-absorbing product.

Example 3

This Example Shows Lengthened Shelf Life of Packaged Jerky at Ambient Temperatures To demonstrate how well the present invention inhibits bacterial growth, an accelerated 12 month test was conducted on a 4 oz. packet of beef jerky. To this sample of beef jerky a one-gram packet of trona/citric acid (9:1 w/w) was added. The beef jerky was contained in a moisture and gas impermeable plastic envelope, and at the conclusion of the accelerated test, the jerky was removed and analyzed using the AOAC 966.23 method and the standard plate count was less than 10 CFU/g. The coliform count was determined using the AOAC 991.14 method, and it was also found to be less than 10 CFU/g. When the *E. Coli* count was determined using the same method, it was also found to be less than 10 CFU/g. Using AOAC 2003.07 method the *Staphylococcus* count was also found to be less than 10 CFU/g. To analyze for *Salmonella* a modified AOAC 998.09 method was used and it was negative in a 25 gram sample. The yeast and mold were less than 10 CFU/g when the FDA BAM method was used. The moisture content was found to be 15.89 wt. % when it was analyzed using a Denver IR-200.

Generally, after an accelerated 12 month test, the jerky would be dry and brittle and the bacterial count would be greatly increased. In this test the moisture content of the jerky packet was essentially the same as when first packaged. The jerky was not hard but pliable. Furthermore, the bacterial counts were comparable, if not less than, when the jerky was first packaged. These tests clearly demonstrate that the oxygen removing capacity of the trona/citric acid prevents the drying out of and controls the bacterial growth on packaged beef jerky.

Example 4

Jerky

To demonstrate how well the present invention inhibits bacterial growth, an accelerated 12 month test was conducted on a 6 oz. packet of beef jerky in a plastic envelope as in Example 3. The only difference was the size of the beef jerky (6 oz.) in the packet. To this sample of beef jerky a one-gram gas permeable packet of trona/citric acid (9:1 w/w) was added. The beef jerky packet was sealed, and at the conclusion of the accelerated test, the jerky was analyzed using the AOAC 966.23 method and the standard plate count was 5500 CFU/g. The coliform count was determined using the AOAC 991.14 method, and it was found to be less than 10 CFU/g. When the *E. Coli* count was determined using the same method it was also found to be less than 10 CFU/g. Using AOAC 2003.07 method the *Staphylococcus* count was also found to be less than 10 CFU/g. To analyze for *Salmonella* a modified AOAC 998.09 method was used and it was negative in a 25 gram sample. The yeast and mold were less than 10 CFU/g when the FDA BAM method was used. The moisture content was found to be 9.82 wt. % when it was analyzed using a Denver IR-200.

As in Example 3 the moisture content of the jerky packet was essentially the same as when first packaged. The jerky was not hard but pliable. Furthermore, the bacterial counts were comparable, if not less than, when the jerky was first packaged. These tests again clearly demonstrate that the oxygen removing capacity of the trona/citric acid prevents the drying out of and controls the bacterial growth on packaged beef jerky.

Example 5

Jerky

To further confirm the results of Examples 3 and 4 on bacterial growth and moisture content of jerky following an accelerated 12 month test, a third test was conducted on a 4 oz. packet of beef jerky. The trona/citric acid content was the same as in Examples 3 and 4. At the conclusion of the tests the bacterial, yeast and mold counts were as reported in Examples 3 and 4. The moisture content of the jerky was found to be 16.46 wt. % when it was analyzed using a Denver IR-200. All of these tests confirm the results of Examples 3 and 4. In other words the oxygen removing capacity of the trona/citric acid prevents the drying out of and controls the bacterial growth on packaged beef jerky.

Example 6

This Example Shows Rapid Cooling of Cooked Chunks of Meat by Means of Trona/Citric Acid Mixtures When large pieces or chunks of meat are cooked, the existing regulations require that such cooked meats are to be cooled from the cooking temperature, about 150° F., to about 45° F. in not more than six hours. In this example, to four tanks, 4'×4'×4', was added 450 gallons of water and 13 blocks of ice (each block weighing about 10 lbs.). To two of the tanks was added two 36 gram packets of trona/citric acid, (9:1 w/w) powder encased in plastic packets permeable to both liquid and gas. Approximately 900 lbs of cooked beef shanks, each shank being about 12 to 15 lbs in weight, and which had been cooked at about 150° F. for about 1.5 hours, was added to each tank. Temperature probes monitored selected pieces of beef shank at 30 minute intervals at the top, center and bottom of each tested shank until an average temperature of 80° F. was reached. The shanks in the tubs containing the trona/citric acid packet reach the 80° F. temperature in an average time of about 1.5 hours whereas the tanks not containing the trona/citric acid the packet took about 2 hours. When the meat reached a temperature of about 60° F. the shanks were removed and placed in a cooler room maintained at 30-35° F. The shanks from the trona/citric acid tank reached the desired temperature of about 45° F. in the cooler room in about 3 hours whereas the meat from the untreated tanks took between 5 and 6 hours.

The difference in time between the trona/citric acid cooled shanks and the plain water cooled shanks results in a significant labor and time savings and also accelerates the efficiency and throughput of meat from cooking to final cooling temperature significantly. The financial gain resulting from increased productivity in a shorter period of time is a major factor in cooked meat production.

Example 7

Perishable Products

In reference to FIGS. 5 and 9, tubes containing packets of trona/acid (9:1 w/w) will enhance the chilling and preservation of perishable products within an oxygen containing environment. The oxygen absorbing capabilities of the trona/acid and the production of carbon dioxide gas stops or slows the growth of spoilage pathogens within such enclosed environment. Susceptible spoilage pathogens are inclusive of bacteria, fungi, viruses, and other microorganisms of animal or vegetable origin. Susceptible environments include, but are not limited to, warehouses or similar storage facilities to keep perishable products fresh and enhance cooling properties; manufacturing plants to absorb heat from ovens, machinery, outside environment; transportation environments to preserve perishable products for extended periods, i.e. days or weeks; crates or containers for shipping overland or overseas to preserve perishable products; refrigerated trucks or reefers to enhance energy efficiency and save on transportation fuel costs while simultaneously chilling and preserving perishable products; maintaining moisture in meats, and produce such as fruits and vegetables.

In general the tubes containing trona/acid packets will extend the life of perishable products such that they maintain freshness, moisture and reduce or eliminate spoilage depending upon the number of packets and the amount of trona/acid within the packets.

Example 8

Perishable Goods

Packets as shown in FIGS. 3 and 4 situated in open and closable containers containing oxygen perishable goods may be used to extend the life of such goods even though there are repeated openings and closings of the containers. This lengthens storage or shelf live even after repeated opening/closing of the package or container for days or weeks and also will permit the container to be made of thinner packaging materials thus reducing costs.

Example 9

Jerky and Dried Fruit

Into a container as shown in FIG. 13 is placed freshly cured jerky and/or dried fruit (e.g. pears, apples, peaches, etc.) along with a packet of trona/acid as shown in FIGS. 3 and 4. The oxygen in the container is absorbed by the trona/acid and replaced by carbon dioxide as a result of the interaction of the trona/acid with the oxygen. The jerky or fruit, when placed in the container, will maintain freshness for about 18 months, or even longer if not subjected to the open atmosphere. The amount of trona/acid will depend upon the volume of the fruit to be treated.

Even with continuous opening and closing, the jerky or dried fruit in the container will remain fresh, i.e. not lose its moisture content, for 30 days or longer due to the presence of the trona/acid packets.

Example 10

Produce

The trona/acid packets in the presence of produce, fruits and vegetables slows the natural decay process which allows such produce to maintain better color, texture and smell for up to 30 days from harvest to point of sale. Even additional days of freshness from the fields to the retailer and in the store may be obtained when produce is properly handled and refrigerated. The trona/acid packets removes oxygen and enhances the production of carbon dioxide ($CO_2$) providing an atmosphere having bacteriostatic properties that helps to retard the growth of spoilage bacteria present on fruits and vegetables.

Particularly when the produce is refrigerated, the endothermic properties of the trona/acid packets will provide an atmosphere which chills harvested food quickly and naturally and extends the freshness of the produce from the fields to the retailer and in the store; extends refrigerated shelf life of the produce; reduces the risk of cross contamination and related liability or the produce; improves the air quality inside refrigerated storage and display cases (See FIG. 9); reduces offensive odors thereby in fewer discards, markdowns and spoilage.

Example 11

Meat

The trona/acid mixture contained in packets is natural, non-toxic products. What is beneficial is that this product, when exposed to the oxygen present on the surface of meat or in the atmosphere surrounding the meat somehow aids in the production of carbon dioxide ($CO_2$), an inert gas known to have bacteriostatic properties. $CO_2$ gas is believed to wrap itself around meat creating an envelope that helps retard the growth of spoilage bacteria present on meats.

By slowing the natural decay process; meats (including red meat, poultry and fish) maintain better color, texture and smell consistent with freshness. This property leads to Consumer takeaway, satisfaction and repeat sales are increased.

Moreover, growers, producers, wholesalers, shippers, manufacturers, processors and retailers will realize immediate benefits when using the combined trona/acid combinations which will (a) extend the freshness from processing and shipping to the warehouse and in the store; (b) extend refrigerated shelf life of red meat, poultry and fish; (c) reduce the risk of cross contamination and related liability of oxygen degradable products; (d) improve the air quality inside refrigerated storage and display cases; (e) reduce offensive odors; and (f) result in the reduction of discards, markdowns and spoilage of oxygen perishable meat products.

Example 12

Warehousing and Storage

When used in refrigerated warehouses and storage units, the combined trona/carboxylic acid mixture can change the atmospheric conditions within the enclosed environment to improve efficiencies in cooling. Temperatures are lowered not only on the oxygen degradable produce and meats but within the entire warehouse. This cooling results in enhanced preservation of products along with the ability for products to retain their moisture content thereby keeping the produce fresh over a longer period of time.

The trona/carboxylic acid mixture is a natural and safe product which not only reduces oxygen content within an enclosed atmosphere but also somehow, not fully understood, results in the production of carbon dioxide ($CO_2$), which, when removing oxygen from within the immediate vicinity of oxygen perishable products, may serve as an inert gas having bacteriostatic properties. The carbon dioxide gas settles around the oxygen perishable produce creating an envelope that helps retard the growth of spoilage bacteria present on produce such as red meat, poultry, fish, fruits and vegetables.

By slowing the natural oxidation or decay process in produce; fruits and vegetables there will be maintained a better color, texture and smell of such produce. Some of the advantage attributable to the presence of trona/carboxylic acid packets in sufficient number and strategically located are: (a) extending product freshness in the warehouse; (b) increasing the storage days of products while maintaining fresh meat, fish, produce and dry goods: (c) reducing the risk of cross contamination and related liability: (d) improving the air flow, air quality and circulation inside refrigerated storage and display cases: (e) reducing offensive odors: (e) minimizing discards, markdowns and spoilage: (f) lowering the temperature of food naturally: (g) chilling harvested food products quickly and naturally: and (h) improving the efficiencies of cooling systems thus reducing power costs.

Example 13

Transportation

Packets containing trona/carboxylic acid mixtures, in appropriate amounts and strategically spaced within a cargo space will protect oxygen perishable goods shipped long distances, i.e. from one country to another, cross country, and by various means of transportation, such as air cargo, ships, railway, trucks and any other means. If appropriately utilized and spaced the trona/carboxylic acid packets will increase the sustainability of such oxygen perishable products and add additional days or even weeks of freshness. By placing trona/carboxylic acid packets in pallets with product or in the shipping area, it will keep the product cool, maintain moisture in products, minimize or remove oxygen in the environment and surround products with carbon dioxide which, in such an environment possesses bacteriostatic properties.

When shipping produce under such conditions the shipper can add extra days of freshness when transporting produce, meats and fish, increase geographical coverage with additional days while keeping perishables fresh. By slowing the natural decay process in meats, fish and produce during shipping and transportation, foods stay fresher longer and arrive in the stores with longer shelf life and less spoilage. As a result the moisture content of the produce will be maintained, the risk of cross contamination and related liability will be reduced, the air quality inside the storage area will be improved and offensive odors reduced. The result will be to extend the sustainability and freshness of perishable products from the fields to the retailer and to the stores, the produce will arrive at the final destination with less spoilage and fewer discards, and there will be an increased area of geographical coverage with additional days while keeping perishables fresh.

Example 14

Growers

Growers and producers of fruits and vegetables have found that they may preserve their products immediately upon being picked and/or harvested by the use of the trona/carboxylic acid filled packets of this invention. As previously stated this trona/acid combination protects oxygen perishable produce and also results in enhancing an environment of carbon dioxide ($CO_2$), which has been shown to have bacteriostatic properties. Fruits and vegetables are cocooned or enclosed in the stable environment protected by the trona/acid combination which allows this such produce to retain its moisture content and remain in a picked or harvested state.

By slowing the natural decaying process in produce during harvesting, storage and shipping, which is attributed to the presence of oxygen, foods stay fresh longer and arrive at stores with increased shelf life and reduced spoilage.

Example 15

Home Storage/Refrigeration

Within an enclosed atmosphere, such as a refrigerator or pantry, the trona/carboxylic acid, when appropriately placed in oxygen permeable packets will extend the freshness of oxygen perishable products for up to about one month. In this regard it will extend the shelf life and retard the growth of bacteria that may be present on meats, jerky, dried fruit, and produce.

By slowing the natural decay process in produce; fruits and vegetables maintain better color, texture and smell. Other advantages to be found are that it will (a) extend the freshness of opened food in enclosed areas up to 30 days; (b) improve the air quality inside home refrigerators and pantries; (c) be ideal for home food storage and long term emergency preparedness; (d) reduce the risk of cross contamination or various produce items; (e) reduce offensive odors; and (f) result in less produce spoilage and fewer discards.

Example 16

Pharmaceuticals

Pharmaceuticals, particularly tablets or capsules, are usually packaged in larger containers for shipment from the manufacturer to a pharmacy or other intermediary. From there the pharmaceuticals may be dispensed as is or divided into smaller containers to pharmacies, hospitals, nursing homes, extended care facilities. If a prescription item, the pharmaceuticals may be further dispensed in smaller containers. If marketed without a prescription and are placed on a shelf in the pharmacy, supermarket, or other retail outlet for the consumer to purchase they are still considered to be pharmaceuticals for purposes of this invention. In each of these events the tablets or capsules are subjected to an open environment numerous times which may be detrimental to the viability and stability of the pharmaceutical. This allows the pharmaceutical to be subjected to an oxygen atmosphere. It is not unusual to have a silica gel or similar packet present in the container to absorb moisture but the oxygen content in the surrounding atmosphere is not reduced.

By placing an appropriate amount of trona/carboxylic acid packets in the container the oxygen present within the container will be absorbed and the stability of the pharmaceuticals will be enhanced. The container having the trona/carboxylic acid packets will provide an oxygen free environment within its confines and will continue to absorb oxygen and provide a carbon dioxide ($CO_2$), environment within the pharmaceutical container for days and even weeks although the container may be repeatedly opened and closed as the tablets or capsules within are dispensed. Furthermore, the packets additionally reduce moisture content and can function as a desiccant which can further extend shelf-life of sensitive pharmaceutical products.

Example 17

Red Blood Cell Transfusions

Although transfusions can be lifesaving, they are not without risk. In critically ill patients, red blood cell (RBC) transfusions are associated with increased morbidity and mortality, which may increase with prolonged RBC storage before transfusion. Red blood cells can be stored from 21 to 42 days if kept refrigerated at 33.8 to 42.8° F. (1 to 6° C.) and an approved preservative is added. The mean storage time before transfusion in the United States is 17 days. This shelf life can be extended if packets of these red blood cells are kept in the presence of trona/acid packets (as shown in FIG. 3). The oxygen absorbing capabilities and the production of carbon dioxide gas stops or slows the growth of pathogens, which help prevent storage lesion—a set of biochemical and biomechanical changes which occur during storage within such enclosed environment. Current regulatory measures are in place to minimize red blood cell, RBC, storage lesion—including a maximum shelf life (currently 42 days), a maximum auto-hemolysis threshold (currently 1% in the US), together with an average 24-hour post-transfusion RBC survival in vivo of more than 75%. These regulatory measures are exceeded when red blood cells are stored in the usual manor in the presence of trona/acid mixture.

Example 18

Whole Blood Transfusions

Whole blood, unseparated venous blood, can be stored for up to 35 days if kept refrigerated at 33.8 to 42.8° F. (1 to 6° C.) and an approved preservative is added. This shelf life can be extended if packets of this whole blood are kept in the presence of trona/acid packets (as shown in FIG. 3). The oxygen absorbing capabilities and the production of carbon dioxide gas stops or slows the growth of pathogens, which help prevent storage lesion—a set of biochemical and biomechanical changes which occur during storage within such enclosed environment. The storage lesions are reduced by the presence of trona/acid and the transfusion efficacy in a patient is improved. In general the presence of trona/acid packets will extend the shelf life of whole blood so that it can be used in blood transfusions, and these blood transfusions will have greater efficacy.

Example 19

Plasma Transfusions

Plasma and fractionated plasma products benefit by storage in the presence of trona/acid packets (as shown in FIG. 3). The oxygen absorbing capabilities and the production of carbon dioxide gas stops or slows the growth of pathogens. These conditions increase the shelf life, and improve the transfusion efficacy in a patient.

Example 20

Organ Transplants

Because most transplanted organs are from deceased donors, the organ must inevitably be stored after its removal from the donor until it can be transplanted into a suitable recipient. The donor and recipient are often in different locations, and time is needed to transport the donor organ to the hospital where the recipient is being prepared for transplantation. Effective, safe, and reliable methods are needed to preserve the organ ex vivo until transplantation can be performed. Acceptable preservation times vary with the organ. Most surgeons prefer to transplant the heart within 5 hours of its removal; the kidney can safely be stored for 40-50 hours, but earlier transplantation is preferred. Most pancreas transplants are performed after 5-15 hours of preservation. Liver transplantations usually are performed within 6-12 hours. Hypothermia is the preferred technique of organ preservation because it is simple, does not require sophisticated expensive equipment, and allows ease of transport. Hypothermia is beneficial because it slows metabolism. Organs exposed to normothermic ischemia remain viable for relatively short periods, usually less than 1 hour. However, biodegradable reactions continue; these include the accumulation of lactic acid, a decrease in intracellular pH, proteolysis, lipolysis, and lipid peroxidation. The oxygen absorbing capabilities and the production of carbon dioxide gas as disclosed herein stops or slows the growth of pathogens, which help prevent storage lesion—a set of biochemical and biomechanical changes which occur during storage within such enclosed environment. In the presence of trona/acid (FIG. 3) the conditions are improved, and the preservation of organs ex vivo can be extended until transplantation can be performed.

It should be understood that the foregoing disclosure relates to exemplary embodiments of the invention and that modifications may be made without departing from the spirit and scope of the invention as set forth in the claims that follow.

The invention claimed is:

1. A composition for extending the life of oxygen perishable products comprising a granular mixture of a sodium carbonate mineral and citric acid.

2. The composition according to claim 1, wherein the sodium carbonate mineral is a member selected from the group consisting of trona, gaylussite, natron, prissonite, northupite, nahcolite, thermonatrite, and combinations thereof.

3. The composition according to claim 2, wherein the sodium carbonate mineral is trona.

4. The composition according to claim 3, wherein the trona comprises the formula

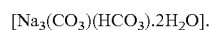
[$Na_3(CO_3)(HCO_3).2H_2O$].

5. The composition according to claim 1, wherein the sodium carbonate mineral is trona and a w/w ratio of trona to citric acid is 200:1 to 5:1.

6. The composition according to claim 1, wherein the composition is a granular composition contained in a gas permeable packet.

7. The composition according to claim 1, wherein the granular mixture is oriented within a beverage stopper.

8. The composition according to claim 1, wherein the oxygen perishable goods is a member selected from the group consisting of fruits, vegetables, flowers, fresh and cooked meats, processed foods, whole kernel grains, processed grains, grain flour, dosage form pharmaceuticals, whole blood, blood products, harvested transplantable organs, and combinations thereof.

9. A composition for extending the life of oxygen perishable products comprising a granular mixture of a sodium carbonate mineral and an acid which is a mono-, di- or tricarboxylic acid, wherein the composition is a granular composition contained in a gas permeable packet.

10. The composition according to claim 9, wherein the mono-, di- or tricarboxylic acid has the general formula:

(HOOC)—R—(COOH)$_{x-1}$ where x is an integer of 1, 2 or 3, and R is a saturated or unsaturated, straight, or branched carbon chain having one to eighteen carbon atoms, or an aromatic moiety having six to eighteen carbon atoms which may be unsubstituted or substituted by OH, COOH, COOM, COOR', —OR' substituents, where M can be an alkali or alkaline earth metal, and where R' can be saturated or unsaturated, straight, or branched carbon chain having from one to eight carbons, an aromatic moiety having six to eighteen carbon atoms which may be substituted by alkyl groups having one to eight carbons, OH, COOH, COOM, COOR', —OR' substituents, and M can be an alkali or alkaline earth metal.

11. The composition according to claim 10, wherein, the acid is a member selected from the group consisting of citric acid and salicylic acid.

12. The composition according to claim 10, wherein the acid is citric acid.

13. The composition according to claim 9, wherein the sodium carbonate mineral is a member selected from the group consisting of trona, gaylussite, natron, prissonite, northupite, nahcolite, thermonatrite, and combinations thereof.

14. The composition according to claim 9, wherein the sodium carbonate mineral is trona.

15. The composition according to claim 9, wherein the acid is citric acid and the sodium carbonate mineral is trona and a w/w ratio of trona to citric acid is 200:1 to 5:1.

* * * * *